United States Patent [19]

Kobuke

[11] 4,174,319

[45] Nov. 13, 1979

[54] 12-ALKYL-1,4,7,10-TETRAAZACYCLOTRI-DECANE

[75] Inventor: Yoshiaki Kobuke, Kyoto, Japan

[73] Assignee: Iwao Tabushi, Kyoto, Japan

[21] Appl. No.: 871,349

[22] Filed: Jan. 23, 1978

[30] Foreign Application Priority Data

May 19, 1977 [JP] Japan .................................. 52/57125

[51] Int. Cl.² .......................................... C07D 257/02
[52] U.S. Cl. ................................ 260/239 BC; 423/2;
423/6; 423/24
[58] Field of Search .................................. 260/239 BC

[56] References Cited

U.S. PATENT DOCUMENTS

| B,403,326 | 1/1976 | Richman ........................ 260/239 BC |
| 3,828,023 | 8/1974 | Cornier et al. ................ 260/239 BC |
| 3,860,576 | 1/1975 | Ham et al. ..................... 260/239 BC |

Primary Examiner—Glennon H. Hollrah
Assistant Examiner—D. B. Springer
Attorney, Agent, or Firm—Frishauf, Holtz, Goodman & Woodward

[57] ABSTRACT 12-alkyl-1,4,7,10-tetraazacyclotridecane of the formula

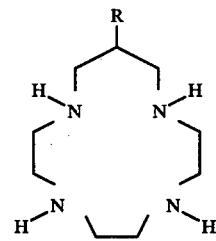

wherein R is an alkyl group containing at least 8 carbon atoms. This compound can be used for capturing metal ions.

3 Claims, 6 Drawing Figures

12-ALKYL-1,4,7,10-TETRAAZACYCLOTRIDECANE

BACKGROUND OF THE INVENTION

1. Field of the Invention

The present invention relates to novel compounds. More particularly it is concerned with 12-alkyl-1,4,7,10-tetraazacyclotridecane which can be used in selectively and efficiently capturing metal ions, for example, metal ions contained in waste water.

2. Description of the Prior Art

Metal ions such as copper, cobalt, nickel, mercury, cadmium, zinc and the like ions contained in waste water have hitherto been removed from the standpoint of preventing pollution. Metal ion capturing agents for use in removing these metal ions include activated carbon, kieselguhr, and the like, which capture the metal ions by physical absorption, and ion exchange resins, chelate resins, and the like, which capture the metal ions by chemical binding action. These metal ion capturing agents, however, are of no practical value since activated carbon, kieselguhr, and the like are insufficient in removing low concentrations of the metal ions, and ion exchange resins are of low selectivity to the metal ions. With regard to chelate resins, since they are of high selectivity to all the heavy metal ions, they are suitable for use in removing all the heavy metal ions from industrial waste water for preventing pollution. These chelate resins, however, have a disadvantage in that since they are of low selectivity to specific metal ions, they cannot be employed in selectively separating, purifying and condensing the specific metal ions from the metal ion mixture in which various kinds of metal ions coexist, for example, in recovery of noble metal and the like.

As a method of separating or condensing uranium from an aqueous solution containing uranium, a solvent extraction method using amines is known. This procedure, however, is markedly disadvantageous from the practical standpoint since it requires a large amount of amines because of their low ability to complex with uranium.

Thus it has long been desired to develop novel materials capable of selectively and effectively capturing metal ions. Based on the discovery that 1,4,7,10-tetraazacyclotridecane has an excellent ability to capture metal ions, but that since said compound is water-soluble, it is difficult to separate and recover the metal ions captured from waste water and the like, it has now been found that introduction of alkyl groups containing 8 or more carbon atoms into the above 1,4,7,10-tetraazacyclotridecane decreases the solubility thereof in water while keeping its excellent capturing ability.

SUMMARY OF THE INVENTION

The present invention provides a novel 12-alkyl-1,4,7,10-tetraazacyclotridecane represented by the formula

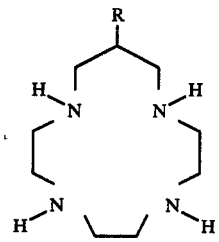

wherein R is an alkyl group containing at least 8 carbon atoms. This compound can be used as a capturing agent for metal ions.

BRIEF DESCRIPTION OF THE DRAWINGS

FIG. 1 (A) is a plane view, and FIG. 1 (B) is a sectional side elevation view;

DETAILED DESCRIPTION OF THIS INVENTION

Figure 1A:
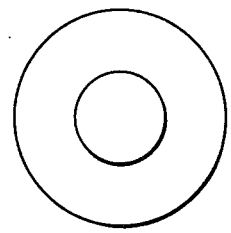
FIG. 1 illustrates a sectional view of a Pressman cell which is used in the Example.

The alkyl group of 12-alkyl-1,4,7,10-tetraazacyclotridecane should be those containing at least 8 carbon atoms. In general, those alkyl groups containing 8 to 20 carbon atoms are preferred. 12-alkyl-1,4,7,10-tetraazacyclotridecane with an alkyl group containing 7 or less carbon atoms introduced thereinto is of high solubility in water and is difficulty separated as oil layer, and thus it is not suitable for use in capturing metal ions.

Hereinafter, a method of synthesizing a novel compound, 12-alkyl-1,4,7,10-tetraazacyclotridecane of the present invention will be explained. Various methods of synthesizing this compound are applicable, and the following is one embodiment of the method.

A long chain alkyl bromide (RBr) containing at least 8 carbon atoms is reacted with diethyl malonate in ethanol in the presence of sodium ethoxide to obtain diethyl alkylmalonate (A).

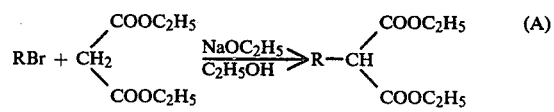

This diethyl alkylmalonate (A) is then reduced with lithium aluminum hydride to obtain diol (B).

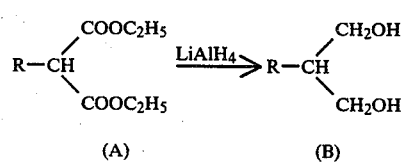

This diol (B) if further reacted with p-toluenesulfonyl chloride (tosyl chloride) to obtain a ditosyl compound (C).

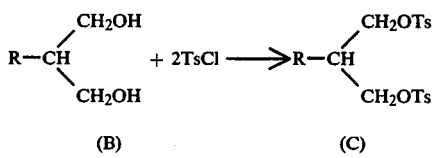

(wherein Ts indicates tosyl group) Thereafter, this ditosyl compound (C) is reacted with a compound (D) prepared by tosylating triethylenetetramine with tosyl chloride, in dimethyl formamide (DMF) in the presence of potassium carbonate to form a cyclic compound (E).

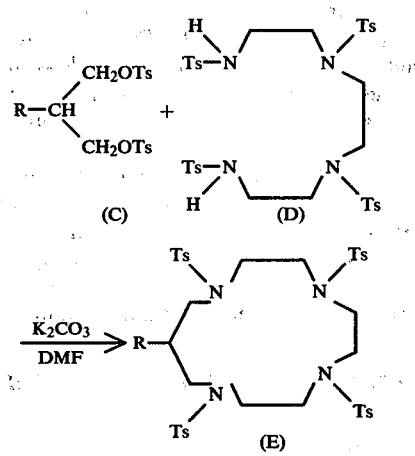

Finally, on removing the tosyl protective groups by hydrobromic acid/phenol, 12-alkyl-1,4,7,10-tetraazacyclotridecane (F), of the present invention is obtained.

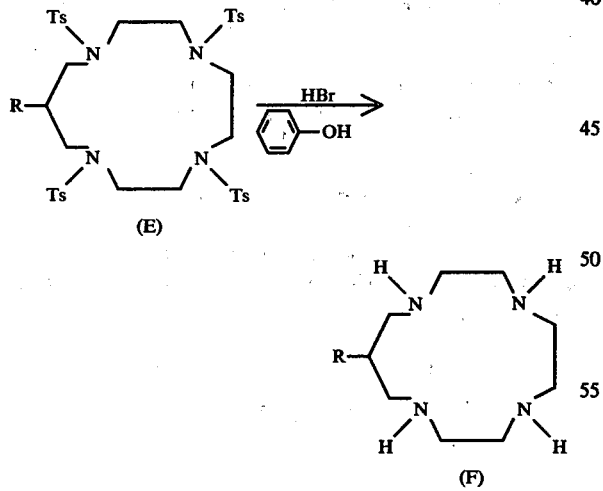

The thus obtained 12-alkyl-1,4,7,10-tetraazacyclotridecane of the present invention is an oil-soluble novel compound. This compound captures metal ions with high selectivity from an aqueous solution quantitatively and at high speeds to extract them in an oil layer.

Removal of metal ions contained in an aqueous solution using the novel compound of the present invention can be carried out by various methods. For example, a novel compound of the present invention is added to an aqueous solution to be treated, at room temperature, and then a neutral solvent such as petroleum ether, benzene, chloroform, methylene chloride, ethyl ether, tetrahydrofuran, ethyl acetate and the like is added thereto to capture the metal ions. The thus formed complex of the novel compound and the metal ion is extracted in the organic solvent layer. For liberating the metal ions from the complex of the novel compound, it is sufficient that an acid is added to the organic solvent and stirring is effected. Therefore, since the novel compound of the present invention is able to efficiently capture metal ions and at the same time, to easily liberate the metal ions captured, it can be recovered by a simple operation after use and re-used.

As apparent from the above explanation, 12-alkyl-1,4,7,10-tetraazacyclotridecane of the present invention can be employed for processing waste water, recovering specific heavy metals from seawater, and further for separating, purifying and condensing metals. In particular, 12-alkyl-1,4,7,10-tetraazacyclotridecane of the present invention is useful for separating and condensing uranium. Therefore, the following explanation will be made to separation and condensation of uranium.

Separation of uranium can be carried out by a liquid film method in which Aqueous Layer I containing uranium ion and Aqueous Layer II containing an uranium removing agent are formed separately from each other. Solvent Layer III containing 12-alkyl-1,4,7,10-tetraazacyclotridecane of the present invention as an uranium carrier is then contacted with Aqueous Layers I and II, and the system so formed is stirred.

Figure 1B:
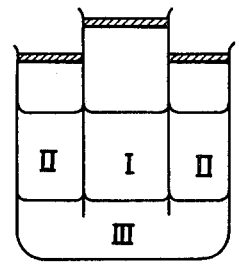
Figure 2:
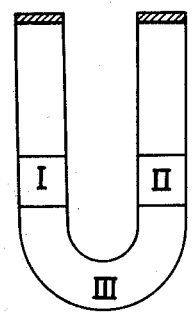
FIGS. 2 and 3 are sectional side elevation views illustrating the states that a water layer and a solvent layer are formed in another cell.
Figure 3:
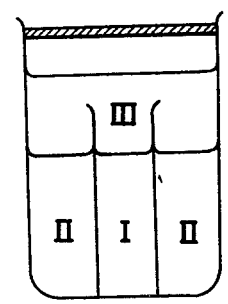

The system to which the above procedure can be applied, is formed by the use of cells as shown in FIGS. 1 to 3.

Aqueous Layer I is an aqueous solution containing an uranium ion and called an uranium stock solution. The concentration of uranium in Aqueous Layer I is not especially limited and a wide range of concentrations can be employed. In general, it is preferred that an uranium stock solution having a concentration of from 1 ppb to $1 \times 10^{-2}$ mole/l be used as Aqueous Layer I.

Aqueous Layer II being formed separately from Aqueous Layer I, must contain an uranium ion removing agent. This uranium ion removing agent acts to liberate an uranium ion from a complex which is formed by capturing the uranium ion in Aqueous Layer I with uranium ion carrier as hereinafter described. As these uranium ion removing agents, inorganic acids such as hydrochloric acid, sulfuric acid, nitric acid and the like are useful. The concentration of the uranium ion removing agent will vary according to the kind of a removing agent being used, the kind and concentration of an uranium ion carrier, the concentration of uranium ion in Aqueous Layer I, etc. In general, a range of from $1 \times 10^{-3}$ mole/l to $1 \times 10^{-1}$ mole/l is preferred.

Layer III is, as described above, formed in such a manner that it is in contact with Aqueous Layers I and II, and it acts as a liquid film separating Aqueous Layers I and II. As mediums for Solvent Layer III, organic solvents, in particular water-insoluble organic solvents such as chloroform, methylene chloride, petroleum ether and the like can be employed.

When the specific gravity of an organic solvent being used is greater than that of water, these layers are formed as shown in FIGS. 1 and 2, whereas when it is less than that of water, the layers are formed as shown in FIG. 3. Solvent Layer III contains an uranium ion carrier, i.e., a material capable of capturing an uranium ion in Aqueous Layer I. The uranium ion carrier as herein used is 12-alkyl-1,4,7,10-tetraazacyclotridecane of the present invention. The compound in which the alkyl group is of 12, 14, 16 or 18 carbon atoms is preferably used.

12-Alkyl-1,4,7,10-tetraazacyclotridecane of the present invention is hydrophobic (oil-soluble) since it has an alkyl group containing a number of carbon atoms, and it has a great ability to capture an uranium ion and form a complex. Furthermore, it has the ability to easily liberate the captured uranium ion by application of an inorganic acid and the like. While the concentration of 12-alkyl-1,4,7,10-tetraazacyclotridecane as an uranium ion carrier in Solvent Layer III varies depending upon various conditions employed, it is sufficient to be in a range of from $1 \times 10^{-5}$ mole/l to $1 \times 10^{-1}$ mole/l.

The mechanism for the separation of an uranium ion according to the above procedure is as follows:

When Aqueous Layer I as an uranium stock solution and Solvent Layer III containing the above described uranium ion carrier are brought in contact with each other, the uranium ion is captured by the carrier and carried to Solvent Layer III as a complex. Next, when Solvent Layer III and Aqueous Layer II containing an uranium ion removing agent are brought in contact with each other, the uranium ion captured by the carrier as a complex in Solvent Layer III is liberated, and carried into Aqueous Layer II and accumulated therein. After the liberation of the uranium ion, the carrier is restored to its former state and re-used. By repeating these procedures, the uranium ion in Aqueous Layer I is carried to Aqueous Layer II and concentrate therein gradually. In particular, it is possible to concentrate the uranium ion more highly by decreasing the amount of water in Aqueous Layer II. Even though Aqueous Layers I and II, and Solvent Layer III are allowed to stand as they are, the transportation of uranium ion proceeds at the contact surfaces between the layers, but its rate is markedly slow. Therefore, it is preferred that the carrying rate of uranium ion is increased by stirring the system comprising the above layers.

As described above, the use of the above described procedure allows the effective separation and concentration of uranium ions from a uranium stock solution of low concentration. Furthermore, since the carrier being used can be employed repeatedly, it is sufficient to use a small amount of the carrier.

Therefore, the above procedure can be effectively employed for production of concentrated uranium. In particular, it is possible to separate a high concentration of uranium from sea-water containing a low concentration of uranium ion. Thus, 12-alkyl-1,4,7,10-tetraazacyclotridecane of the present invention is of quite practical value.

Hereinafter, the present invention will be explained in more detail by reference to the following examples and application examples.

EXAMPLE 1

(1) Preparation of 2-hydroxymethyl-tetradecanol-1

To 40 milliliters of ethanol was added 2.53 grams of sodium gradually. After the sodium was dissolved, 17.5 milliliters of diethyl malonate was added thereto, and the resulting mixture was refluxed for 30 minutes. Into this mixture was gradually dropped 25 grams of lauryl bromide with stirring over a period of 1.5 hours. After the dropping was completed, the mixture was further refluxed for 2.5 hours. After the mixture was cooled, it was neutralized. Then the salt was filtered and the solvent was distilled away. The salt precipitated was again filtered. Thereafter, it was washed with ether, and the solvent was distilled away. Thus, crude diethyl n-dodecyl malonate was obtained.

To the crude compound obtained above was slowly dropped 100 milliliters of dry ether dissolved with 6.46 grams of lithium aluminum hydride therein while cooling with ice. After the dropping was completed, the mixture was refluxed for 2 hours, and then hydrochloric acid-ice water was added thereto. After the mixture was filtered, the precipitate was recrystallized from ethyl acetate, and thus 16.3 grams of 2-hydroxymethyl-tetradecanol-1 was obtained. The yield was 67%. (2) Preparation of ditosyl compound 14.7 grams of 2-hydroxymethyl-tetradecanol-1 obtained by the above procedure (1) was dissolved in 180 milliliters of pyridine and cooled with ice water. Then, 28.6 grams of tosyl chloride was added thereto, and the resulting mixture was stored in a refrigerator for one night. Next day, the mixture was poured into ice-hydrochloric acid and extracted with ether. After the solvent was distilled away, the precipitate was purified by column chromatography (solvent: mixed solvent of benzene-ethyl acetate (3:1)), and thus 29.8 grams of a ditosyl compound in which tosyl groups were bonded to the oxygens of the two hydroxy groups of 2-hydroxymethyl-tetradecanol-1, was obtained. The yield was 90%.

(3) Preparation of N,N',N'',N'''-tetratosyltriethylenetetramine 6.56 grams of triethylenetetramine was dissolved in 100 milliliters of 2 N aqueous solution of sodium carbonate, to which 38.2 grams of tosyl chloride was gradually added over a period of 2 hours keeping the temperature at 65° to 70° C. After the addition was completed, the resulting mixture was stirred at 95° C. for 2 hours, cooled and filtered. The cake-like precipitate was washed with ethanol and filtered, and thus 29.1 grams of white powdery tetratosyl compound, N,N',N'',N'''-tetratosyltriethylenetetramine was obtained. The yield was 85%.

(4) Cyclization reaction 8.2 grams of the ditosyl compound obtained by the procedure (2) and 12.3 grams of the tetratosyl compound obtained by the procedure (3) were dissolved in 50 milliliters of dimethylformamide. The resulting mixture was slowly dropped into a mixture of 7.1 grams of potassium carbonate and 40 milliliters of dimethylformamide at a temperature of 100° to 110° C. over a period of 8 hours. The mixture was further heated at 140° to 160° C. for 18 hours, and then neutralized with hydrochloric acid. The solvent was distilled away. The thus obtained residue was purified by column chromatography (solvent: mixed solvent of benzene-ethyl acetate (3:1)), and thus 9.50 grams of a cyclic compound, N,N',N'',N'''-tetratosyl compound of 12-n-dodecyl-1,4,7,10-tetraazacyclotridecane was obtained. The yield was 76%.

(5) Removal of tosyl protective groups

One gram of the cyclic compound obtained by the procedure (4) was heated with 2.5 grams of phenol and 45 milliliters of hydrobromic acid at 140° C. for 5 hours. After the mixture was cooled, it was subjected to ether extraction to remove black by-products. The aqueous layer was made alkaline and again subjected to ether extraction. The ether was then distilled away. Then the remaining solution was distilled at 150° C./0.01 mmHg in Kugelrohr distillation apparatus, and thus 0.3 gram of 12-n-dodecyl-1,4,7,10-tetraazacyclotridecane, which had no tosyl protective group, was obtained. The yield was 87%.

The analytic results of the compound obtained above were as follows:

Elemental Analysis:

|   | Calculated($C_{21}H_{46}N_4$) (%) | Found (%) |
|---|---|---|
| C | 71.13 | 70.88 |
| H | 13.07 | 13.42 |
| N | 15.80 | 15.68 |

Infrared Analysis (KBr tablet method): 3350 cm$^{-1}$ ($\nu$NH), 2920 cm$^{-1}$ ($\nu_{as}$ CH), 2850 cm$^{-1}$ ($\nu_s$ CH), 1460 cm$^{-1}$ ($\delta_{as}$ $CH_2$), 1350 cm$^{-1}$ ($\delta CH_3$), 1280 cm$^{-1}$ ($\nu CN$)

NMR Analysis (Solvent: $CDCl_3$): $\delta$ 3.83 (4H, NH), $\delta$ 2.84 (16H, $CH_2$—N), $\delta$ 1.22, $\delta$ 0.86 (26H, $CH_2CH_3$)

Others: White powder; Melting point: 86° to 88° C.; Molecular weight: 354,

Structural Formula:

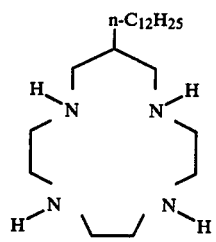

Application Example 1

Heavy metal ions such as mercury ions, cadmium ions and the like contained in waste water in quite low concentrations were separated and concentrated by a liquid film transportation method in which 12-n-dodecyl-1,4,7,10-tetraazacyclotridecane obtained in Example 1 was used as a carrier. This procedure was conducted in a Pressman cell as shown in FIG. 1 wherein a heavy metal salt and a removing agent were introduced into Aqueous Layers I and II, respectively, and the carrier was stored in Chloroform Layer III and stirred at a constant speed. Samples were withdrawn from Aqueous Layers I and II, and their heavy metal ion concentrations were measured by atomic-absorption spectroscopy.

Selectivities of the above carrier to the heavy metal ions in its carrying properties were measured using 0.1 N hydrochloric acid as a removing agent of aqueous layer II and found to be in the order:

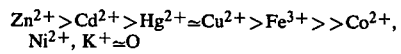

$Zn^{2+}$ and $Cd^{2+}$ were carried positively. On the other hand, metal ion absorption abilities of the carrier were measured by the distribution method and found to be in the order:

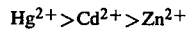

Thus, it was found that the carrying speed mainly depends on the removing speed of a metal ion from the complex of the carrier and the metal ion.

Figure 4:
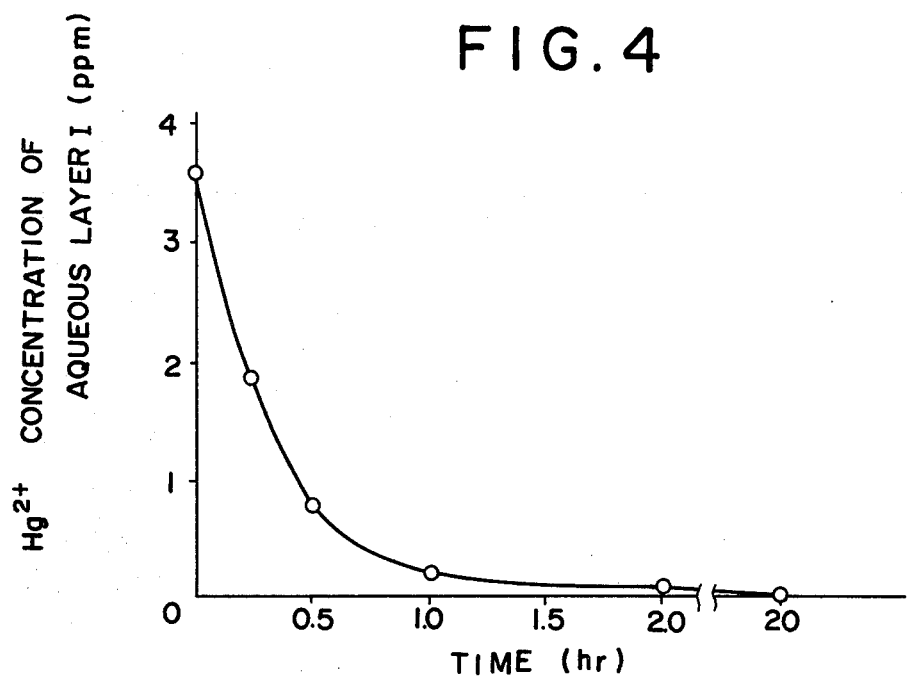
FIGS. 4 and 5 are graphs showing a change in $Hg^{2+}$ concentration with a lapse of time in water layer I when transportation is carried out using sodium hydrogenborate in the Example, the carrier (12-n-dodecyl-1,4,7,10-tetraazacyclotridecane) concentration being $1\times10^{-3}$ mole/l and $1\times10^{-4}$ mole/l in FIGS. 4 and 5, respectively.
Figure 5:
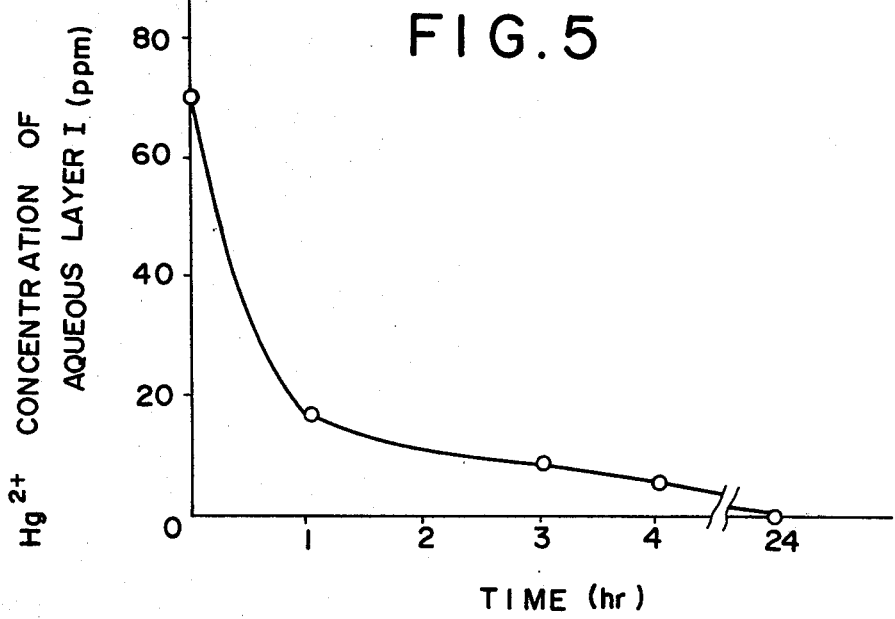

When reducing agents such as ascorbic acid, sodium hydrogenborate, and the like were used as removing agents, it was possible to separate mercury ions into Aqueous Layer II as metallic mercury. FIGS. 4 and 5 show a reduction in $Hg^{2+}$ concentration of Aqueous Layer I when the transport was effected using sodium hydrogenborate. FIG. 4 indicates that even though a dilute solution (the initial concentration of $Hg^{2+}$: 3.7 ppm) was used, the concentration of $Hg^{2+}$ was reduced to about 1/10 of the initial concentration with a contact time of one hour and the concentration after 20 hours was reduced to 0 to 0.01 ppm. As can be seen from FIG. 5, even though an aqueous mercury solution having a higher concentration (initial concentration of $Hg^{2+}$: 70 ppm) and the concentration of 12-n-dodecyl-1,4,7,10-tetraazacyclotridecane was reduced to 1/10, the same tendency as above was observed, and it was indicated that the carrier was turned over. In the cases of FIGS. 4 and 5, the mercury ion ($Hg^{2+}$) was contacted with the reducing agent contained in Aqueous Layer II and precipitated as metallic mercury (Hg).

As described above, the use of a novel compound of the present invention, 12-n-dodecyl-1,4,7,10-tetraazacyclotridecane as a capturing agent (carrier) enables concentration and separation of mercury, cadmium and zinc against the concentration gradient by the use of a positive carrying method using an apparatus as shown in FIG. 1. In particular, the concentration of mercury can be reduced below the limit of detection.

Application Example 2

In this example, a Pressman cell (made of glass; inner diameter: 23 millimeters; outer diameter: 35 millimeters) was used. An uranium stock solution ($3\times 10^{-3}$ mole of uranium ion/liter of the solution) was contacted with Solvent Layer III, chloroform containing $1\times 10^{-3}$ mole/liter of 12-n-dodecyl-1,4,7,10-tetraazacyclotridecane obtained in Example 1 as a carrier. This Solvent Layer III was contacted with Aqueous Layer II containing 0.1 N hydrochloric acid as a removing agent. Thereafter, Solvent Layer III was stirred with a magnetic stirrer to effect the carriage of uranium ions.

The operation was conducted for 2 days at room temperature, during which samples were withdrawn from Aqueous Layers I and II and their uranium ion concentrations were measured by chelate titration and atomic-absorption spectroscopy.

As the uranium ion concentration of Aqueous Layer I gradually decreased, the uranium ion concentration of Aqueous Layer II increased. After 2 days, the ratio of uranium ion concentrations in Aqueous Layers I and II was Aqueous Layer II/Aqueous Layer I=5.0/1.0

What is claimed is:

1. 12-alkyl-1,4,7,10-tetraazacyclotridecane represented by the formula:

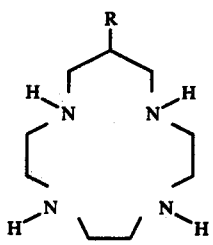
wherein R is a normal alkyl group having from 8 to 20 carbon atoms.
2. The compound according to claim 1, wherein R is a 12, 14, 16, or 18 carbon atom alkyl group.
3. The compound according to claim 1, wherein the compound is represented by the formula:
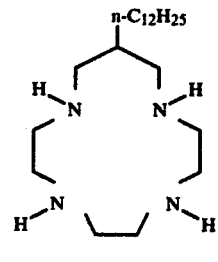
* * * * *